United States Patent [19]
Anahara

[11] Patent Number: 5,674,388
[45] Date of Patent: Oct. 7, 1997

[54] APPARATUS FOR FRACTIONATING COMPONENTS IN LIQUID CHROMATOGRAPHY

[75] Inventor: Seijiro Anahara, Nagoya, Japan

[73] Assignee: Biologica Co., Aichi-ken, Japan

[21] Appl. No.: 598,940

[22] Filed: Feb. 9, 1996

Related U.S. Application Data

[62] Division of Ser. No. 317,869, Oct. 4, 1994, Pat. No. 5,520,817.

[30] Foreign Application Priority Data

Dec. 20, 1993 [JP] Japan .................................. 5-320236

[51] Int. Cl.⁶ ................................................. B01D 15/08
[52] U.S. Cl. ................................ 210/198.2; 210/656
[58] Field of Search .............................. 210/635, 656, 210/659, 198.2; 422/70; 436/161; 73/61.56

[56] References Cited

U.S. PATENT DOCUMENTS

| | | | |
|---|---|---|---|
| 3,621,263 | 11/1971 | Gilson | 250/218 |
| 4,019,545 | 4/1977 | Vinatieri | 141/130 |
| 4,040,940 | 8/1977 | Bier | 204/299 R |
| 4,083,690 | 4/1978 | Inoue | 426/231 |
| 4,116,046 | 9/1978 | Stein | 210/198.2 |
| 4,171,715 | 10/1979 | Forsstrom | 141/130 |
| 4,483,773 | 11/1984 | Yang | 210/198.2 |
| 4,577,492 | 3/1986 | Holba | 210/198.2 |
| 4,659,568 | 4/1987 | Heilman | 530/417 |
| 4,714,554 | 12/1987 | Ito | 210/635 |
| 5,462,660 | 10/1995 | Singleton | 210/659 |

FOREIGN PATENT DOCUMENTS

| | | | |
|---|---|---|---|
| 5264532 | 10/1993 | Japan | 210/198.2 |

*Primary Examiner*—Ernest G. Therkorn
*Attorney, Agent, or Firm*—Dennison, Meserole, Pollack & Scheiner

[57] ABSTRACT

Apparatus for fractionating components separated in liquid chromatography is disclosed. The apparatus includes a sample applying section, a column section, a detector section, and a tubing line connecting the sections. The apparatus further includes a fractionation tube for fractionating eluent portions containing prospective components separated from the column, an air injector for injecting air into the fractionation tube, and a valve for a switching operation such that either of the eluent fed through a flow path or air fed through an air flow path from the air injector is led into the fractionation tube while the other is drained to the drain side.

4 Claims, 3 Drawing Sheets

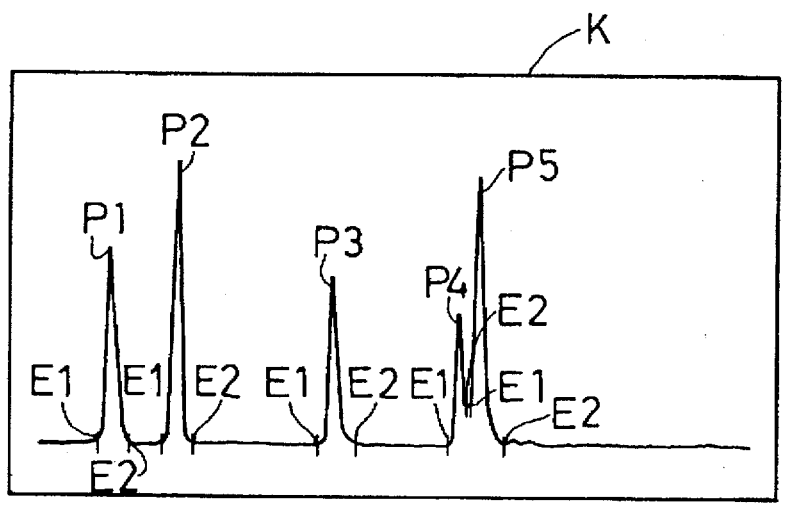
FIG. 3(A)
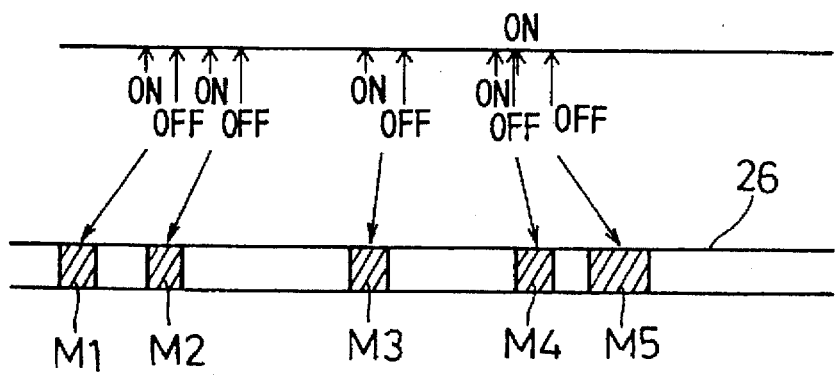
FIG. 3(B)
FIG. 3(C)

APPARATUS FOR FRACTIONATING COMPONENTS IN LIQUID CHROMATOGRAPHY

This is a division of Ser. No. 08/317,869, filed Oct. 4, 1994, now U.S. Pat. No. 5,520,817.

BACKGROUND OF THE INVENTION

1. Field of the Invention

This invention relates to a method of and an apparatus for fractionating components in liquid chromatography (hereinafter abbreviated as LC).

2. Description of the Prior Art

In general, the LC is a method of separating various components in a sample by applying the sample into a separation column while causing an eluent (or eluate) to flow continuously into the column. Usually, a detector for optically detecting each separated component is disposed on the column outlet side, and a recorder is connected to the detector. Each component detected in the detector is electrically measured in a photoelectric tube or the like to produce electric indication, which is transmitted to the recorder to be recorded continuously as a graph on a chart paper in the recorder.

When fractionating components separated in the conventional LC for the purposes of other tests or the like, the eluent from the detector is led to an apparatus so called fraction collector to obtain solution containing the separated components in a test tube of the collector.

When separating a small amount of component in a small volume of sample, capillary column liquid chromatography (hereinafter abbreviated as CCLC) is used particularly. However, the volume of solution containing a component separated and obtained by the CCLC is very small, for instance 1 to 10 µl, and it is difficult and almost impossible to reliably fractionate such a small amount of liquid into a test tube of the fraction collector used in the conventional LC. Besides; the amount of liquid corresponding to one peak on the chromatogram is very small, and by causing the liquid to be dropped as drops into the test tube for fractionation, the detected component that is condensed in the column chromatography is diluted.

As a method for solving this problem, the inventor has earlier invented a "Method of Blotting Components in Capillary Column Liquid Chromatography" (disclosed in Japanese Laid-Open Patent Publication No. 5-264352). This disclosed invention features that an eluent containing detected components led out from the column, is successively adsorbed onto an adsorbing sheet disposed in a chromatograph. More specifically, instead of dropping the eluent from a chromatography flow path end, the eluent is continuously blotted onto the adsorbing sheet. The necessary portions of the resultant adsorbing sheet are cut out and preserved to permit very small amounts of detected components to be extracted faithfully to the detected component separation status.

In this method, however, the eluent is blotted on the adsorbing sheet. This means that it is necessary to extract the component from the adsorbing sheet in a subsequent treatment. Therefore, there arise problems in the man-hour of the extracting operation and the efficiency of the extraction. In addition, a technique is needed to obtain efficient adsorption of the component on the adsorbing sheet. The method, therefore, is not always convenient for the subsequent treatment. Further, when the spots of components are close to one another, it is sometimes difficult to select the cutting positions of the adsorbing sheet.

SUMMARY OF THE INVENTION

It is, accordingly, an object of the present invention to provide a novel method of and apparatus for fractionating components in LC in which eluent containing components separated from a column is not dropped from the lower end of a flow path but is fractionated in a tube connected to the flow path such that its portions containing the respective components are separated from one another by intervening air.

Another object of the invention is to provide a novel method of and apparatus for fractionating components in LC which permits fractionation of components such that the fractionated components are reliably separated from one another and can be conveniently handled.

To attain the above objects of the invention, there is provided a method of fractionating components in LC, which comprises the steps of applying a sample to a column filled with a separation media while supplying an eluent to the column, causing eluent portions containing components in the sample to flow into a fractionation tube connected to the end of an eluent flow path, holding the eluent portions in the fractionation tube, and injecting air into a rear portion of the eluent in the fractionation tube.

According to the invention, there is also provided an apparatus for fractionating components in LC including a sample applying section, a column section, a detector section, and a tubing line connecting these sections, which comprises a fractionation tube for fractionating eluent portions containing respective components separated from the column, air injecting means for injecting air into the fractionation tube, and a valve for switching operation such that either of the eluent fed through a flow path from the column or air fed through an air flow path from the air injecting means is led into the fractionation tube while the other is drained to the draining side.

Since the eluent is not dropped from LC flow path end but the eluent portions are fractionated as a flow and continuously in the fractionation tube, it is possible to fractionate reliably and accurately very small volume of eluent portions that can not be formed into drops. Further, since the eluent portions can be fractionated in the state of liquid, no extracting operation is needed in the subsequent treatment. Each eluent portion containing a component can be held in the fractionation tube such that it is separated from the eluent portion of the next elution by air introduced into the fractionation tube subsequent to it.

The present invention will be more fully understood from the following detailed description and appended claims when taken with the accompanying drawings.

BRIEF DESCRIPTION OF THE DRAWINGS

FIG. 3(A) is a chromatogram, FIG. 3(B) is a view showing a corresponding peak detection signal from a peak sensor, and FIG. 3(C) is a view showing a corresponding status of eluent portions containing detected components in a fractionation tube.

DETAILED DESCRIPTION OF THE PREFERRED EMBODIMENT

A preferred embodiment of the invention will now be described with reference to FIGS. 1, 2 and 3(A) to 3(C). In this embodiment, the invention is applied to a case of CCLC to separate and fractionate a plurality of different proteins contained in a sample.

Figure 1:
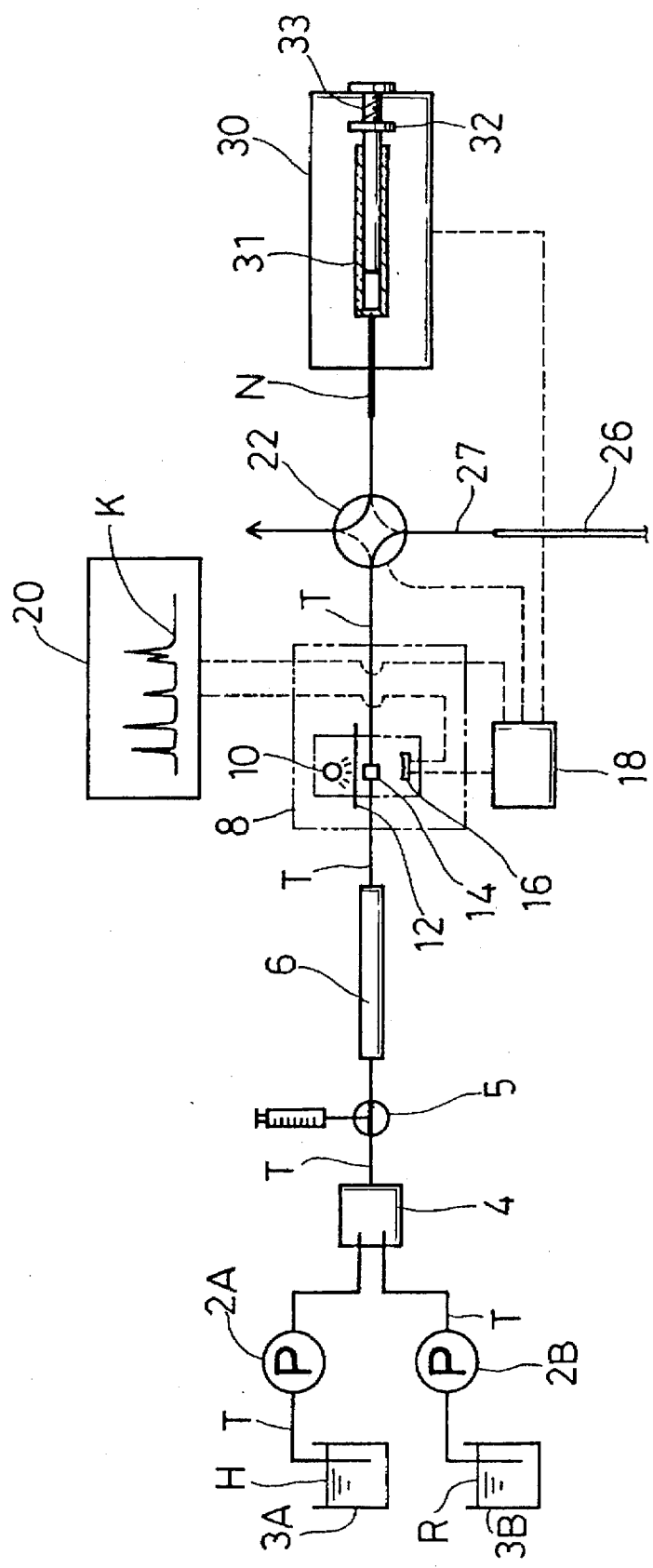
FIG. 1 is a schematic representation of an apparatus according to an embodiment of the invention.

FIG. 1 is a schematic representation of the CCLC adopted in the embodiment and the overall apparatus construction for fractionating components in a sample separated in the CCLC. As shown in FIG. 1, the CCLC apparatus includes eluent tanks 3A and 3B, pumps 2A and 2B for pumping out eluent, a mixer 4, an injector valve 5, a column 6 for separating components in the sample, a detector 8 for detecting the components separated from the sample, and a recorder 20.

These components are suitably connected together by capillary tubes T so that the eluent flows through these parts in the mentioned order.

The eluent has an action of causing elution of sample components adsorbed to a separation media in the column 6. It may be selected from those which are normally used in LC. For example, it may be a mixed solution composed of two liquid components, for instance water and acetonitrile. In such case, the ratio of the two liquid components is adjusted suitably or in accordance with the lapse of the analysis time.

The column 6 may be any ordinary column used for CCLC. Particularly, it is suitable to use a capillary tube with an inner diameter of, for instance, 180 to 320 µm. The column 6 used in this embodiment comprises a tube which is 320 µm in inner diameter and 15 cm in length and which is filled with a separation media in the form of fine particles mainly composed of silica gel. The separation media comprises fine particles which can bond (adsorb) sample components and which can be adequately eluted with the eluent. As an example, silica gel fine particles may be used, in which Alkyl chains, such as Octa Desyl chain, having hydrophobisity in water are introduced into their surface.

The detector 8 used in this embodiment is a spectrophotometer ("SC-100, flow cell UZ-LI type" manufactured by Spectraphysics Inc., in U.S.A.). The detector 8 includes a light source 10, a filter 12, a flow cell 14 and a light-receiving section 16. Light from the light source 10 is passed through the filter 12 to illuminate the eluent passing through the flow cell 14.

The recorder 20 receives a signal from the light-receiving section 16 and records a chromatogram K on a recording sheet or the like. The recorder 20 also receives a peak detection start signal and a peak detection end signal from a peak sensor 18 to be described later for recording event marks E1 and E2 corresponding to the peak detection start and end signals together with peaks on the chromatogram K as shown in FIG. 3(A).

As shown in FIG. 1, the fractionation apparatus provided in the CCLC system mainly comprises a peak sensor 18, a change-over valve 22, a fractionation tube 26 and air injecting means 30.

The peak sensor 18 receives an electric signal representing the absorbance measured by the light-receiving section 16 in the detector 18, and it detects the elution of a light-absorbing component from an absorbance increase or like change based on a preset light absorption wavelength. It transmits the detection signal to the valve 22, the recorder 20 and the air injecting means 30.

Figure 2:
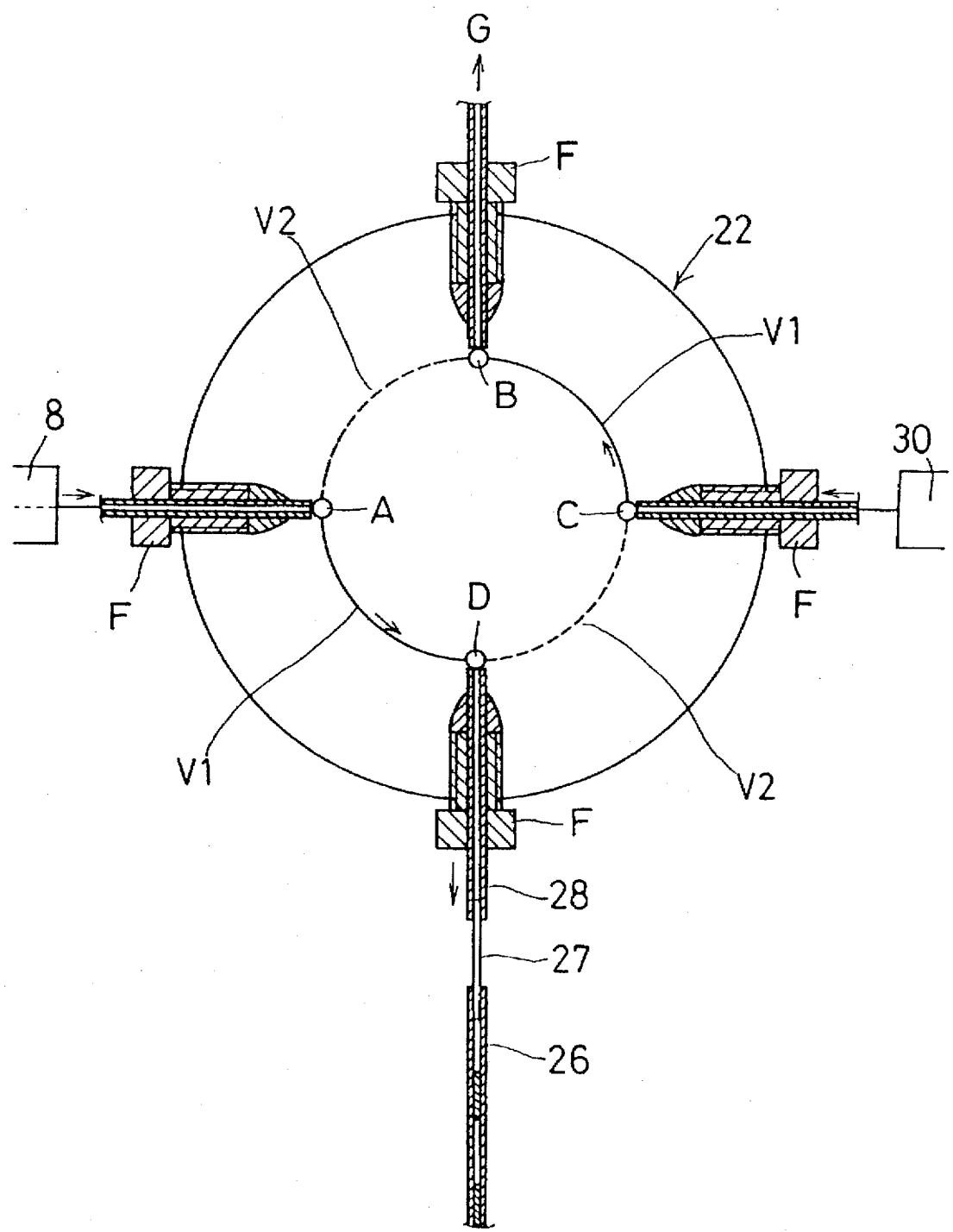
FIG. 2 is a view showing port switching directions in a change-over valve in the apparatus shown in FIG. 1.

FIG. 2 shows the change-over valve 22. As shown, the valve 22 has four switchable ports A to D. The port A is connected via a ferrule F to an eluent flow path from the detector 8. The port B is likewise connected to a draining path for draining eluent. The port C is likewise connected to the air injecting means 30. The port D is connected to the fractionation tube 26.

The valve 22 can switch, in response to the operation of an electromagnetic switch according to the electric signal from the peak sensor 18, the eluent from the port A to the draining path G at the port B or to the flow path to the fractionation tube 26 at the port D. Further, the valve 22 can switch air from the port C to the fractionation tube 26. Specifically, while no peak is being detected, the eluent is led to the draining path G. While a peak is being detected, on the other hand, the eluent is led into the fractionation tube 26.

The fractionation tube 26 has an elongate tubular shape open at both ends. The material and shape of the fractionation tube 26 are such that it can hold eluent portions containing components in it. It may have a curved or bent portion. The fractionation tube 26 used in this embodiment is a Teflon tube with an inner diameter of 250 µm ("Teflon" is the trademark for polytetrafluoroethylene). The Teflon tube is such that its inner surface is hydrophobic and it can readily hold the eluent in it with the surface tension. Thus, the eluent held in this fractionation tube 26 can be retained in its held condition even if the fractionation tube 26 is bent or shaken.

The fractionation tube 26 is connected to the port D of the valve 22 via a fused silica tube 27 with an inner diameter of 50 µm and an outer diameter of 280 µm, and via a thin tube 28 fitted on the fused silica tube 27 and inserted into the ferrule F. This connecting way is effective for precluding dead volume which would be otherwise created by a connector and preventing the dispersion of the fractionated liquid. In addition, it is possible to make ready mounting and dismounting and permit convenient handling. Further, the fractionation tube 26 is conveniently transparent so that the positions of eluent portions fractionated in the fractionation tube 26 can be readily determined.

As shown in FIG. 1, the air injecting means 30 of this embodiment includes a gas tight syringe 31 with a rod 32 capable of being advanced by a thread 33 into the syringe 31. The syringe 31 has a needle N connected at its extreme end to the port C of the valve 22. The air injecting means 30 receives an electric signal from the peak sensor 18 and leads air at a preset flow rate into the fractionation tube 26 through the port C and a flow path V1 in the valve 22. Further, as soon as a peak detection end signal is sent from the peak sensor 18, the air injecting means 30 forces out a few microliters of air into the fractionation tube 26.

Now, an example of use of the above CCLC system and the fractionation apparatus for CCLC will be described.

Before injecting a sample into the system, eluent is caused to flow through the system for sufficient substitution of the system flow path space. In this embodiment, the eluent is a mixture of distilled water H and acetonitrile R, as shown in FIG. 1. After the sample injection, the proportion of acetonitrile R is increased progressively with the lapse of the analysis time, and the eluent is caused to flow at a constant rate of, for instance, 1 to 10 µl /min. Further, the detector 8 and so forth are stabilized by energization before the sample injection.

A sample in a syringe is injected into the injector valve 5 to be led with the eluent toward the column 6. The sample entering the column 6 together with the eluent is adsorbed and de-adsorbed with respect to the separation media, so that the individual components are separated and eluted from the column 6. Thus, the eluent after the lapse of a preset period of time from the instant of the sample injection, contains the individual components.

The eluent emerging from the column 6 enters the flow cell 14 in the detector 8 and is exposed by light beam of a preset wavelength passed through the filter 12. The light-receiving section 16 detects light passed from the flow cell 14 and measures the absorbance. The measurement value is converted to an electric signal and is transmitted to the recorder 20 and the peak sensor 18. In the recorder 20, the received absorbance data are successively recorded as a chromatogram K in a preset scale on a recording sheet.

FIG. 3(A) shows the chromatogram K, FIG. 3(B) shows the status of peak detection by the peak sensor 18, and FIG. 3(C) shows eluent portions M1 to M5 in the fractionation tube 26. In FIGS. 3(A) to 3(C), the chromatogram K, the peak detection status and the eluent portions M1 to M5 in the fractionation tube 26 are shown in correspondence to one another.

The peak sensor 18 detects electric signal changes as a peak if a peak detection level which is set in compliance with analyzing and fractionating conditions is exceeded, but it does not detect any peak if the peak detection level is not exceeded. Thus, while no protein component is eluted after the sample injection, a no peak detection state prevails. In this state, the flow path V1 In the valve 22 is off, and the eluent is led through the valve 22 to the draining path G to be drained.

Subsequently, when a protein component is eluted, the electric signal from the detector 8 is increased in level, and the peak sensor 18 detects this electric signal change as a peak P1. The peak sensor 18 thus transmits an on signal to activate the valve 22. As a result, the valve 22 is switched to a flow path V2, as shown in FIG. 2, thus leading the eluent portion M1 from the flow cell 14 to the fractionation tube 26. Actually, the eluent portion containing the protein component arrives at the valve 22 after the lapse of a certain period of time after the detection of the elution of the protein component the flow cell 14. Accordingly, a preset delay time set between the peak detection by the peak sensor 18 and the operation of the valve 22.

Meanwhile, as shown in FIG. 3(A), the signal is simultaneously transmitted to the recorder 20. Thus, an event mark E1 indicative of the start of peak detection is recorded together with the peak P1 on the chromatogram K in the recorder 20.

When the level of the electric signal received by the peak sensor 18 becomes lower than the peak detection level, the detection of signal as peak P1 is discontinued, and a peak detection end signal is outputted. Thus, after a preset delay time, the valve 22 is switched to the flow path V2 shown in FIG. 2. Then, the eluent not containing any component is again drained through the draining path G, and air is introduced into the fractionation tube 26 at a time. In this way, only the protein-containing eluent portion M1 is fractionated in the fractionation tube 26.

Meanwhile, the peak detection end signal is transmitted to the recorder 20, so that a peak detection end event mark M2 is recorded on the chromatogram K (see FIG. 3(A)).

In a preset period of time after the elution corresponding to the first peak P1, elution corresponding to a second peak P2 takes place, and then, after the lapse of a preset period of time, elution corresponding to a third peak P3 occurs. The eluent portions M1 to M3 corresponding to the peaks P1 to P3 are fractionated in the fractionation tube 26 such that they are separated from one another by air introduced between adjacent elution times (see FIG. 3(C)).

The fractionation of the components corresponding to fourth and fifth peaks P4 and P5 will now be described.

With the elution of the fourth protein from the column 6, the absorbance detected by the light-receiving section 16 is increased. The peak sensor 18 detects this absorbance change as a peak P4, and a peak detection start signal is provided to the valve 22 and the recorder 20. As in the previous cases of the peaks P1 to P3, the valve 22 is switched upon reception of the peak detection start signal, and the eluent portion M4 is introduced into the fractionation tube 26. As soon as the detection of the fourth peak P4 is ended, a peak P5 is detected with elution of the fifth protein.

In this case, while the valve 22 is switched according to the signals that are generated, because of a very short period of time between the fourth peak detection end signal and the fifth peak detection start signal, sufficient air can not be introduced into the fractionation tube 26 with the normal air injection rate. In this case, the fourth and fifth eluent portions M4 and M5 may not be sufficiently separated from each other in the fractionation tube 26.

For this reason, if the time interval between the peak detection end signal and the subsequent peak detection start signal is within a preset period of time, the air injecting means 30 forces out air more quickly than usual. With this function, a distance can be secured between the fourth and fifth eluent portions M4 and M5 in the fractionation tube 26 (see FIG. 3(C)).

The eluent portion M5 corresponding to the fifth peak P5 is fractionated in the fractionation tube 26. After the end of the analysis, the fractionation tube 26 is removed from the fused silica tube 27.

As shown in FIGS. 3(A) to 3(C), the eluent portions M1 to M5 corresponding to the peaks P1 to P5 recorded together with the event marks E1 and E2 therefor on the chromatograph K, are held in the removed fractionation tube 26 successively such that they are separated in correspondence to the inter-peak intervals on the chromatogram K. Since the fractionation tube 26 is transparent, it is readily possible to confirm the position of each detection component and the correspondence thereof to the chromatogram K.

The individual eluent portions M1 to M5 are held by surface tension in the fractionation tube 26, and their mutually separated state can be held as such even when the fractionation tube 26 is wound or shaken vertically, which is convenient for the handling. Further, the components can be preserved together with the fractionation tube 26. Also, they may be preserved in a frozen state.

When carrying out amino acid analysis or the like of the proteins in the fractionated eluent portions M1 to M5, the fractionation tube 26 may be cut apart at its air-filled portions between adjacent ones of the portions filled with the eluent portions M1 to M5 to obtain cut tube portions individually containing the respective eluent portions M1 to M5.

As shown above, the eluent portions M1 to M5 are fractionated continuously and in the form of liquid without dropping the eluent from the eluent flow path T. The component fractionation method is thus a novel method in LC.

In addition, the method, unlike the one in which eluent is adsorbed to an adsorbing sheet for extraction, there is less possibility of denaturing, decomposition and loss of protein, and there is no need of extracting operation.

Further, it is possible to obtain components in LC effectively and in a condensed state, thus permitting the subsequent treatments to be carried out quickly and without waste.

Further, even peaks P4 and P5 which are close to one another on the chromatogram K can be reliably separatedly fractionated with the switching of the valve 22 and momentary air injection.

Further, it is possible to separatedly fractionate the eluent portions M1 to M5 corresponding to the peaks P1 to P5 without correspondence to the chromatogram K. Further, since the fractionation tube 26 is transparent, the spots to be cut apart can be clearly grasped.

While in the above embodiment, the peak detection is always monitored with the peak sensor 18 for automatically operating the valve 22, this is by no means limitative. For example, where it can be preliminarily known that eluent flows out at a preset rate under preset analysis conditions, the valve 22 can be switched at a preset interval without having resort to the peak sensor 18 but by setting a timer. Further, the valve 22 can be switched manually.

Further, while in the above embodiment, a constant amount of air is introduced from the air injecting means 30 into the fractionation tube 26 whenever a no peak detection state takes place, but this is by no means limitative. For example, it is possible to arrange such that after fractionation of an eluent portion in the fractionation tube 26, a constant amount of air such as to obtain separation of that eluent portion from the next eluent portion may be introduced.

The eluent portions M1 to M5 are taken out from the fractionation tube 26 by cutting the tube 26 and withdrawing each eluent portion from each cut tube using a syringe. Alternatively, air is injected from one end into the fractionation tube 26 from one end thereof, and the eluent portions M1 to M5 are successively withdrawn from the end with a syringe or caused to flow down.

Further, it is possible to introduce the fractionated eluent portions M1 to M5 directly into a mass spectral apparatus or a peptide sequencing apparatus.

As has been described in detail in the foregoing, in the fractionation method according to the invention, eluent portions containing respective components in a sample separated in LC can be fractionated separately without dropping the eluent from the eluent flow path end into the fractionation tube and by injecting air into the fractionation tube during the no peak detection interval of time. This method is a novel method permitting ready and accurate fractionation of each eluent portion containing a component irrespective of the amount of the eluent portion and also permitting reliable fractionation of the components in a condensed state. In addition, with an eluent containing a plurality of different components, the eluent portions containing the individual components can be fractionated accurately.

Further, the invention provides a novel fractionation apparatus in LC which permits fractionation of eluent portions containing components accurately irrespective of the amounts of the eluent portions through valve switching and which permits reliable fractionation of the components in a condensed state.

While the invention has been described with reference to a preferred embodiment thereof, it is to be understood that modifications or variations may be easily made without departing from the scope of the present invention which is defined by the appended claims.

What is claimed is:

1. An apparatus for fractionating eluent portions separated by a liquid chromatography apparatus including a column section for separating a sample into eluent portions each containing a component of the sample, and a detector for detecting components in the eluent portions, said apparatus comprising:

an air injection means;

a fractionation tube for fractionating separated eluent portions;

a valve having four ports, a first port connected to the liquid chromatography apparatus for receiving eluent portions, a second port connected to said fractionation tube, a third port connected to said air injection means and a fourth port connected to a drain; and a valve controller for connection to the detector for communicating the first port with the second port and the third port with the fourth port while the detector detects at least one component, and for communicating the second port with the third port and the first port with the fourth port while the detector does not detect any component.

2. The apparatus of claim 1 wherein the column section is a capillary column.

3. The apparatus of claim 1 wherein the detector section comprises a preset detector at a preset detection level for detecting the eluent portions.

4. The apparatus of claim 3 including means for transmitting an electrical signal to the valve when an eluent portion containing a component is the detector.

* * * * *